United States Patent [19]

Klein et al.

[11] Patent Number: 5,641,816

[45] Date of Patent: Jun. 24, 1997

[54] PROCESS FOR THE PRODUCTION OF POLYOL COMPOUNDS

[75] Inventors: Johann Klein, Duesseldorf; Peter Daute, Essen; Udo Hees, Mayen; Bernd Beuer, Monheim, all of Germany

[73] Assignee: Henkel Kommanditgesellschaft auf Aktien, Duesseldorf, Germany

[21] Appl. No.: 468,149

[22] Filed: Jun. 6, 1995

Related U.S. Application Data

[62] Division of Ser. No. 182,112, Mar. 25, 1994.

[30] Foreign Application Priority Data

Jul. 25, 1991 [DE] Germany ............... 41 24 665.9

[51] Int. Cl.⁶ .................................................. C08G 18/04
[52] U.S. Cl. .................. 521/155; 521/170; 521/172; 521/174; 528/57; 528/74.5; 528/85; 528/295.5
[58] Field of Search ................................ 521/155, 170, 521/172, 174; 528/295.5, 57, 74.5, 85

[56] References Cited

U.S. PATENT DOCUMENTS

| 4,256,847 | 3/1981 | Spector | 521/117 |
| 5,142,020 | 8/1992 | Kud et al. | 525/437 |

*Primary Examiner*—James J. Seidleck
*Assistant Examiner*—John M. Cooney, Jr.
*Attorney, Agent, or Firm*—Wayne C. Jaeschke; John E. Drach; Henry E. Millson, Jr.

[57] ABSTRACT

A process for the production of polyol compounds by condensation of glycerol in the presence of lithium compounds and, optionally, subsequent transesterification of the oligoglycerol mixtures obtained with fatty acid glyceride esters and to their use for the production of polymers.

6 Claims, No Drawings

PROCESS FOR THE PRODUCTION OF POLYOL COMPOUNDS

This application is a Divisional Application of prior U.S. application Ser. No. 08/182,112 filed Mar. 25, 1994.

BACKGROUND OF THE INVENTION

1. Field of the Invention

This invention relates to a process for the production of polyol compounds by condensation of glycerol in the presence of lithium compounds and, optionally, subsequent transesterification of the oligoglycerol mixtures obtained with fatty acid glyceride esters and to their use for the production of polymers.

2. Statement of Related Art

Polyurethanes are produced by reaction of diisocyanates with compounds containing at least two free hydroxyl groups. Polyol compounds used for the production of such plastics include, for example, ring opening products of epoxide compounds with alcohols [Fette, Seifen, Anstrichmitt., 89, 147 (1987)]. Oligoglycerol mixtures are also suitable in principle for this application. However, since the self-condensation of glycerol is normally carried out in the presence of strong bases, more particularly in the presence of sodium or potassium hydroxide, the resulting technical oligoglycerol mixtures generally have a high residual alkali content which can be extremely troublesome in the polyurethane reaction and could lead to unwanted shrinkage of the plastics obtained. The further reaction of the oligoglycerol mixtures with fats and oils to form so-called transesterification polyols or uralkyds, which are also suitable as raw materials for the production of polyurethanes, is also problematical for the same reason. Accordingly, it has hitherto been necessary to free oligoglycerol mixtures from salts with considerable effort before any further reaction.

The problem addressed by the present invention was to provide a new process for the production of polyols based on self-condensation products of glycerol which would be free from the disadvantages mentioned above.

DESCRIPTION OF THE INVENTION

The present invention relates to a process for the production of polyol compounds which is characterized in that a) glycerol is condensed in the presence of lithium compounds,
b) the water of reaction is continuously distilled off and
c) the oligoglycerol mixture obtained is optionally transesterified with fatty acid glyceride esters.

It has surprisingly been found that the self-condensation of glycerol known per se can even be carried out with extremely small quantities of catalyst providing lithium compounds, more particularly lithium hydroxide, are used as the catalyst. The invention is based on the observation that the concentration of alkali in the oligoglycerol mixtures produced by the process according to the invention is so low that neither the polyurethane reaction nor the resulting plastics are adversely affected. The invention also includes the observation that the content of lithium compounds in the oligoglycerol mixtures is sufficient to catalyze subsequent transesterification with fatty acid glycerides, so that there is no need to use an additional transesterification catalyst.

Besides lithium hydroxide, suitable lithium compounds are lithium soaps, i.e. salts of lithium with optionally hydroxyfunctionalized fatty acids containing 6 to 22 carbon atoms and 0, 1, 2 or 3 double bonds. Typical examples are the lithium salts of caproic acid, caprylic acid, capric acid, lauric acid, myristic acid, palmitic acid, palmitoleic acid, stearic acid, oleic acid, elaidic acid, petroselic acid, linoleic acid, linolenic acid, 12-hydroxystearic acid, ricinoleic acid, arachic acid, gadoleic acid, behenic acid or erucic acid. Lithium salts of unsaturated fatty acids are liquid at normal temperature and are therefore easy to dose. Accordingly, they are preferably used. The lithium soaps may be directly added to the reaction mixture. However, they may also be produced in situ, for example from lithium hydroxide and a fatty acid or fatty acid ester.

The quantity in which the lithium compounds are used may be from 0.001 to 0.1% by weight and is preferably from 0.002 to 0.05% by weight and more preferably from 0.005 to 0.01% by weight, based on the glycerol. Since lithium ions are capable of exchange with the alkali metal ions present in glasses, which can lead to a reduction in the concentration of lithium ions, it is advisable to carry out the process in reactors of steel or similarly inert materials.

To carry out the condensation reaction, glycerol and lithium compounds may be initially introduced and heated in an inert gas atmosphere to temperatures of 200° to 300° C. and preferably to temperatures of 220° to 280° C. To displace the equilibrium, it is advisable to remove the water of condensation formed, for example through a water separator.

In cases where it is desired to produce an oligoglycerol mixture of high diglycerol content, it is of advantage to terminate the condensation reaction when the quantity of water theoretically required for the formation of diglycerol has been separated. The reaction time is generally 1 to 30 h and preferably 3 to 15 h. If desired, the diglycerol may be removed from the oligoglycerol mixture formed, for example by distillation in a high vacuum. However, there is generally no need for this purification step.

After the condensation reaction, the oligoglycerol mixtures may be subjected to transesterification with fatty acid glyceride esters.

Suitable fatty acid glyceride esters are triglycerides corresponding to formula (I):

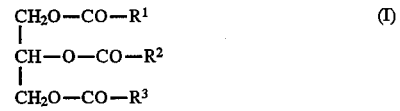

in which $R^1CO$ is a linear or branched aliphatic acyl radical containing 16 to 24 carbon atoms and 1 to 5 double bonds and $R^2CO$ and $R^3CO$ independently of one another represent a linear or branched aliphatic acyl radical containing 6 to 24 carbon atoms and 0 or 1 to 5 double bonds.

The molar ratio of oligoglycerol mixture to fatty acid glyceride ester may be 5:1 to 1:5 and is preferably 3:1 to 1:3. The transesterification may be carried out in known manner at temperatures in the range from 200° to 280° C. The lithium concentration remaining in the oligoglycerol mixture is sufficient also to catalyze the transesterification. Accordingly, there is no need to add other catalysts. The transesterification may be complete, but is generally partial, for example from 10 to 90% by weight and, more particularly, from 20 to 70% by weight, based on the fatty acid glyceride ester.

In one preferred embodiment of the invention, the condensation and transesterification reactions may be carried out in a single step rather than successively.

The present invention also relates to the use of the polyol compounds obtainable by the process according to the invention for the production of polymers in which they may be present in quantities of 1 to 90% by weight and preferably in quantities of 10 to 70% by weight, based on the polymers.

INDUSTRIAL APPLICATIONS

The polyol compounds obtainable by the process according to the invention are suitable as raw materials for the production of polymers. They may be incorporated in alkyd resins by condensation, for example via the hydroxyl groups, and represent structural polycondensation units which are important in particular for the development of polyurethane foams.

The following Examples are intended to illustrate the invention without limiting it in any way.

EXAMPLES

Example 1

In a 2-liter three-necked flask equipped with an internal thermometer and water separator, 1.5 g (0.06 mole) of lithium hydroxide, corresponding to 0.12% by weight—based on the glycerol, were added to 1200 g (13 moles) of glycerol. The reaction mixture was heated under nitrogen for 8 h to 260° C., a quantity of 120 ml of condensate being separated. After cooling, approximately 1000 g of the oligoglycerol mixture were obtained in the form of a dark clear liquid with the following characteristic data: hydroxyl value 1362, acid value 0.4, Li content 365 ppm.

Example 2

A mixture of 994 g (1.12 moles) of new rapeseed oil (oleic acid content>80% by weight) and 406 g (2.45 moles) of the oligoglycerol mixture of Example 1 was introduced into a 2-liter three-necked flask and transesterified under nitrogen over a period of 5 h at 220° C. The product separated and was transferred to a separation funnel by means of which the phase (approximately 50 g) containing the unreacted oligoglycerol was separated off and discarded. 1300 g of the transesterification product were obtained in the form of a light brown clear liquid which had the following characteristic data: hydroxyl value 336, saponification value 142, acid value 1.3, Li content 82 ppm.

What is claimed is:

1. In a method for the preparation of a polyurethane foam, the improvement wherein the polyol component thereof consists of an oligoglycerol present as a reaction component and which comprises from about 1 to about 90% by weight of the polyurethane foam.

2. The method of claim 1 wherein about 10 to about 70% by weight of the oligoglycerol is present in the polyurethane foam.

3. In a method for the preparation of a polymer, the improvement wherein an oligoglycerol mixture is present as a reaction component thereof, said oligoglycerol mixture resulting from the steps of (a) condensing glycerol in the presence of from about 0.001 to about 0.1% by weight, based on the weight of glycerol, of a lithium catalyst selected from the group consisting of LiOH and a lithium salt of a hydroxy-functionalized fatty acid having from about 6 to about 22 carbon atoms and having 0, 1, 2, or 3 double bonds to form an oligoglycerol mixture and water of reaction; and (b) continuously removing said water of reaction as it is formed.

4. The method of claim 3 wherein said polymer is a polyurethane foam.

5. The method of claim 3 wherein from about 1 to about 90% by weight of the oligoglycerol mixture is present in the polymer.

6. The method of claim 4 wherein from about 10 to about 70% by weight of the oligoglycerol mixture is present in the polyurethane foam.

* * * * *